US009101280B2

(12) United States Patent
Bozzarelli

(10) Patent No.: US 9,101,280 B2
(45) Date of Patent: Aug. 11, 2015

(54) PERINEAL PROBE AND PROCESS FOR MAKING A PERINEAL PROBE

(71) Applicant: BEACMED S.r.L., Portalbera (IT)

(72) Inventor: Pier Luigi Bozzarelli, Portalbera (IT)

(73) Assignee: BEACMED S.R.L., Portalbera (Pavia) (IT)

( * ) Notice: Subject to any disclaimer, the term of this patent is extended or adjusted under 35 U.S.C. 154(b) by 115 days.

(21) Appl. No.: 13/952,079

(22) Filed: Jul. 26, 2013

(65) Prior Publication Data

US 2014/0088590 A1 Mar. 27, 2014

(30) Foreign Application Priority Data

Sep. 21, 2012 (EP) .................................... 12185524

(51) Int. Cl.

| | |
|---|---|
| ***A61B 5/0492*** | (2006.01) |
| ***A61N 1/05*** | (2006.01) |
| ***A61N 1/36*** | (2006.01) |
| *A61B 18/00* | (2006.01) |
| *A61B 18/08* | (2006.01) |

(52) U.S. Cl.

CPC ............ *A61B 5/0492* (2013.01); *A61N 1/0512* (2013.01); *A61N 1/0524* (2013.01); *A61N 1/36007* (2013.01); *A61B 18/082* (2013.01); *A61B 2018/00553* (2013.01); *A61B 2018/00559* (2013.01); *A61B 2562/16* (2013.01); *Y10T 29/49002* (2015.01)

(58) Field of Classification Search

CPC ................... A61B 5/0492; A61B 2018/00553; A61B 2018/00559; A61B 2562/16; A61N 1/0512; A61N 1/0524

USPC .................................. 600/373, 393; 607/138

See application file for complete search history.

(56) References Cited

U.S. PATENT DOCUMENTS

| | | | |
|---|---|---|---|
| 3,800,800 | A | 4/1974 | Garbe et al. |
| 5,456,709 | A | 10/1995 | Hamedi |

FOREIGN PATENT DOCUMENTS

| | | | |
|---|---|---|---|
| EP | 0 505 613 | A1 | 9/1992 |
| EP | 0 938 910 | A2 | 9/1999 |

OTHER PUBLICATIONS

The European Search Report issued for European Application No. EP 12 18 5524, completed on Dec. 19, 2012, three pages.

*Primary Examiner* — Lee S Cohen

(74) *Attorney, Agent, or Firm* — Vorys, Sater, Seymour and Pease LLP; Susanne M. Hopkins

(57) ABSTRACT

A perineal probe (1) is provided mainly extending along a main axis (1*a*) and including at least two electrodes (2) protruding from the axial direction (1*a*), spaced one another and electrically insulated along the axial direction (1*a*), one junction element (3) being apt to mechanically connect the electrodes (2) and mainly extending along the main axis (1*a*), in which at least one of the electrodes (2) includes a seat (20) for the junction element (3) apt to realize a first interlocking coupling (4) between the junction element (3) and the seat (20), the junction element (3) including an inner cavity (30) mainly extending along the main axis (1*a*) and elastically deformable portions (31) apt to realize the first interlocking coupling (4), the probe (1) further including an inner body (5) apt to be inserted into the inner cavity (30) and being apt to hinder the elastic deformation of the deformable portions (31) of the junction element (3) in such a way as to prevent the release of the first interlocking coupling (4).

10 Claims, 4 Drawing Sheets

PERINEAL PROBE AND PROCESS FOR MAKING A PERINEAL PROBE

FIELD OF THE INVENTION

The present invention relates to a perineal probe mainly extending along a main axis and comprising at least two electrodes protruding from the axial direction, spaced one another and electrically insulated along the axial direction, one junction element suitable for mechanically connecting the electrodes and mainly extending along the main axis.

In particular, the invention concerns a particular device for the rehabilitation of the perineum, and a process for making such device. A similar probe is described in patent application U.S. Pat. No. 3,800,800.

DESCRIPTION OF THE PRIOR ART

The rehabilitation of incontinence, through electro-stimulation or perineal feed-backs, presently involves the use either of vaginal (to be inserted into the vagina) or anal probes (to be inserted into the anal sphincter) characterized by the presence of at least two conductive electrodes apt to be transferred to the medical apparatus with which the probe is connected, with stimulating pulses or for detecting electro-myographic signals from the anatomical portions in contact with the same. The conductive electrodes are necessarily separated from each other through insulating parts, usually made of plastics or non-conductive resin.

Presently used perineal probes comprise mainly a rod-like element, provided with two electrodes which are separated from each other and mutually insulated, each of them being connected with a suitable generator, capable of electrically feeding the electrodes themselves.

Such components are mutually welded or bonded, in order to avoid the presence of cracks, and then a possible entry of fluids.

As an alternative, the perineal probes are obtained by molding of metal inserts (over-molding), defining the electrodes of the probe, of a single body being both the base element and the insulator.

The aforementioned known art has some important drawbacks.

One first important drawback is represented by the fact, that the perineal probes obtained through welding or bonding require long production times, due to the considerable manpower work needed, together with the complexity and high mounting precision needed.

Furthermore, in the case of probes made by over-molding, a particularly great material input is required, which then determines a high production cost.

Another non secondary drawback is due to the fact that, due to their high weight, the perineal probes are more easily expelled from the cavity of the patient and are unsuited for "standing" rehabilitation techniques.

In this situation the technical task of the present invention is to design a perineal probe and a method of making a perineal probe which are suitable for substantially obviating the drawbacks cited.

Within such technical task, an important aim of the invention is to provide a method for making a perineal probe, and so a perineal probe characterized by reduced production times.

A further aim of the invention is therefore to design a method for making a perineal probe and a perineal probe with reduced costs.

A further important aim of the invention is to design a perineal probe characterized in that it has a reduced weight and therefore can be better used.

SUMMARY OF THE INVENTION

The technical task and the specific aims are reached by a perineal probe mainly extending along a main axis and comprising at least two electrodes protruding from the axial direction, spaced one another and electrically insulated along the axial direction, one junction element suitable for mechanically connecting the electrodes and mainly extending along the main axis, the at least one of the electrodes comprising a seat for the junction element apt to realize a first interlocking coupling between the junction element and the seat, the junction element comprising an inner cavity mainly extending along the main axis and elastically deformable portions apt to realize the first interlocking coupling, and that it comprises an inner body apt to be inserted in the inner cavity and being apt to prevent for interference the elastic deformation of the deformable portions of the junction element in such a way as to prevent the release of the first interlocking coupling.

BRIEF DESCRIPTION OF THE DRAWINGS

Features and advantages of the invention are explained hereinafter by the detailed description of one preferred embodiment of the invention, with reference to the annexed drawings, in which.

DESCRIPTION OF THE PREFERRED EMBODIMENTS

With reference to the Figures mentioned, the perineal probe according to the invention is generally indicated with reference 1. It is suitable for being inserted into the vaginal cavity, and for being electrically connected with an apparatus at the outside of the probe, apt to actuate the same.

Figure 3:
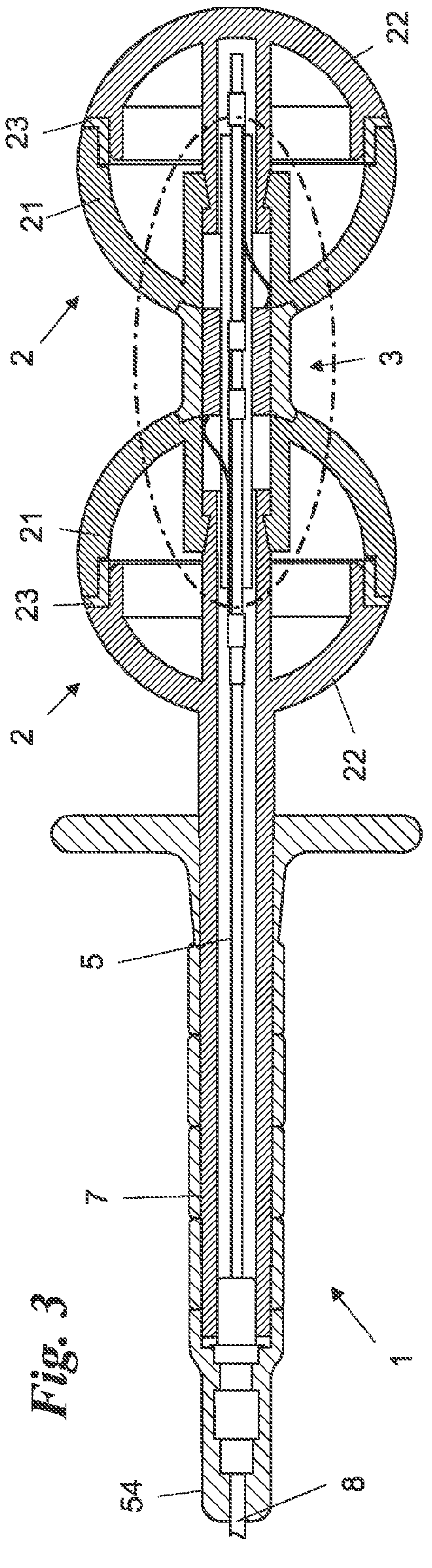
FIG. 3 illustrates out a sagittal section of the probe.

The perineal probe 1 is mainly extended along a main axis 1*a*, and is substantially rod-shaped comprising at least two electrodes 2 protruding from the main axis 1*a*. The perineal probe 1 further defines a front plane 1*b*, which is the section plane of FIG. 4 and on which the main axis 1*a* lies, a sagittal plane 1*c*, which is the section plane of FIG. 3, is perpendicular to the front axis 1*b* and on which the main axis 1*a* lies, and a plurality of transversal planes, perpendicular to the main axis 1*a*.

The probe 1 further briefly comprises: a junction element 3 suitable for mechanically connecting the electrodes 2 and mainly extending along the axial direction 1*a*, a handle 7, also mainly extending along the main axis 1*a*, and apt to be manually grabbed and outer electrical connections 8, apt to connect the probe 1 with the control apparatus outside the probe 1, and substantially made of electrical wires. More particularly the electrodes 2 make on one hand the terminal part opposed to the handle 7 of the probe 1 and on the other hand an intermediate portion of the probe 1, interposed between the handle 7 and the junction element 3.

The electrodes 2 have suitably a substantially spherical or elliptical shape or similar.

Figure 4:
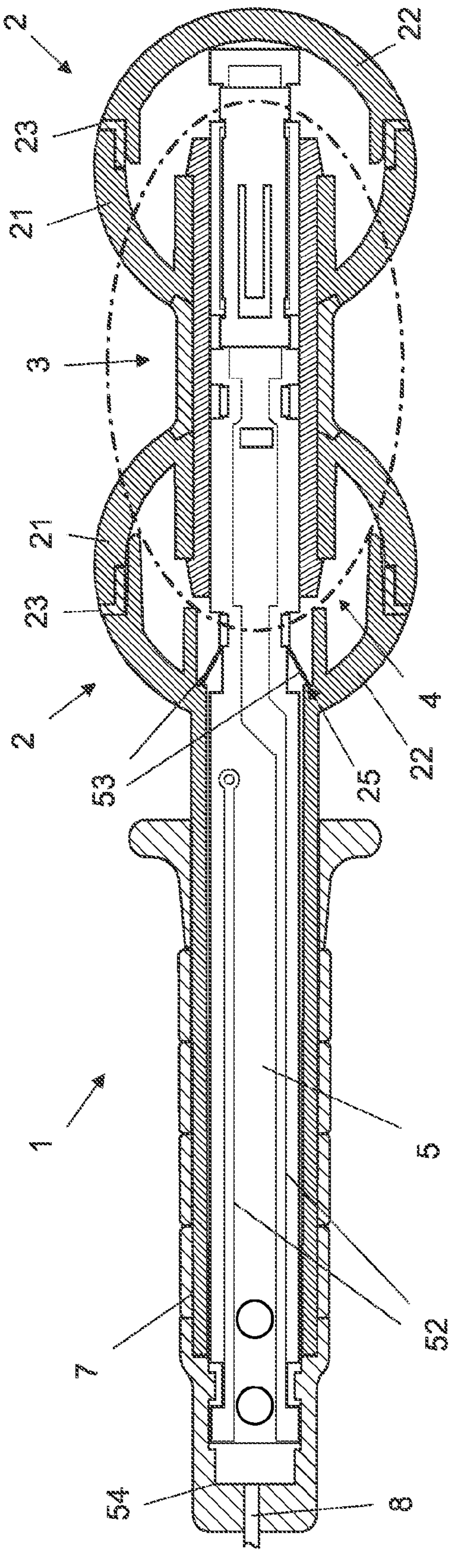
FIG. 4 shows a front section of the probe.
Figure 4A:
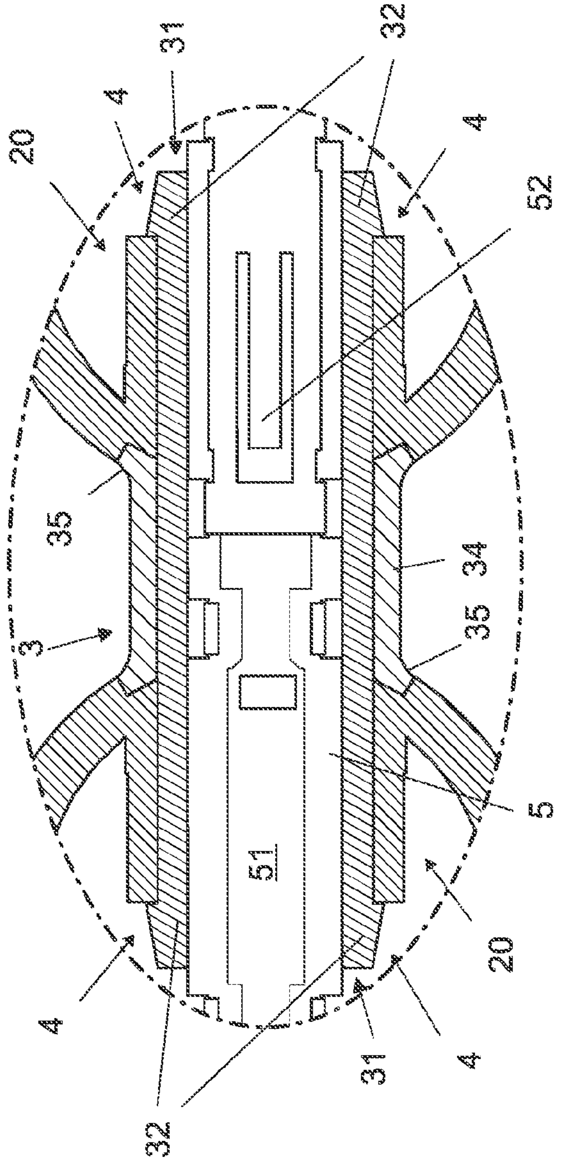
FIG. 4*a* is a magnification of FIG. 4.

Furthermore at least one of the electrodes 2, and preferably both of them, comprises a seat 20 for the junction element 3 apt to make a first interlocking coupling 4 between the junction element 3 and the seat 20 (FIG. 4*a*).

To this end, the junction element 3 comprises elastically deformable portions 31 apt to make the first interlocking coupling 4. Such elastically deformable portions 31 are preferably made of two arms 32 made of a polymeric material, mainly extending parallel to the axis 1*a* and aligned along the front plane 1*b*, which is the section plane of FIG. 4.

Said arms 32 are spaced along the front plane 1*b* and are deflectable towards the interior of the element 3, in order to permit the first interlocking coupling 4. They are finally provided with interlocking teeth facing outward.

The arms 32 are suitably placed along both sides of the central element, in order to make first interlocking couplings 4 with both electrodes 2.

The junction element 3 also comprises an inner cavity 30 mainly extending along the main axis 1*a* and having preferably an elliptical section in the transversal plane, or even trapezoidal, its main axis lying on the front plane 1*a*.

Figure 5:
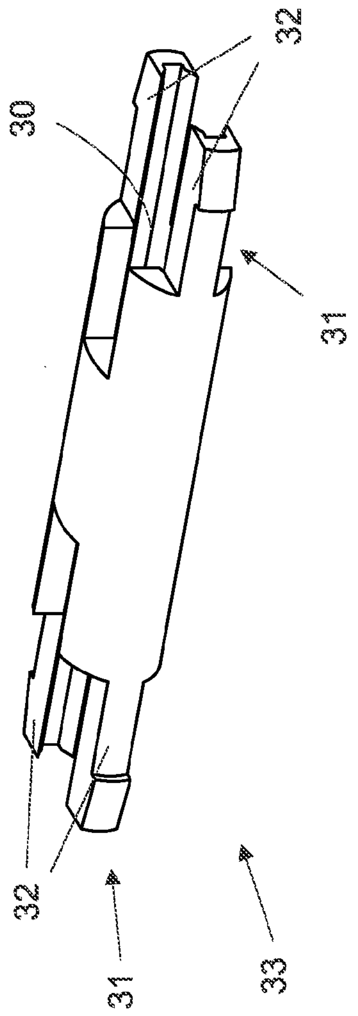
FIG. 5 is a detail of the probe.
Figure 2:
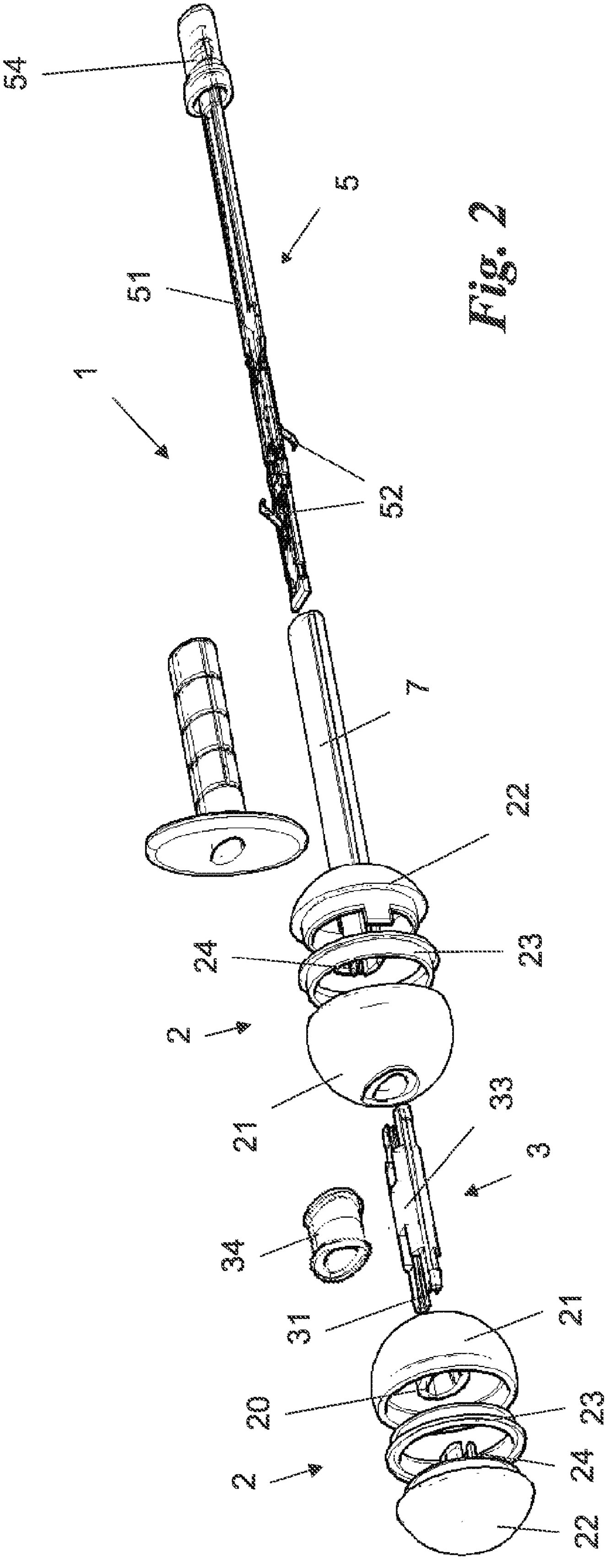
FIG. 2 shows the perineal probe in an exploded view.

The junction element 3 finally comprises a hollow sealing portion 34 and a connecting portion 33 (shown in FIG. 5), which is apt to be inserted into the sealing portion 34. In particular the connecting portion 33 is apt to mechanically connect the two electrodes 2, comprises the arm 31 and is made of a substantially rigid polymeric material. On the contrary, the sealing portion 34 is made of a flexible or soft material and is suitable for warranting a liquid-tight connection between the junction element 3 and the electrodes 2. It is further fastened preferably on two recesses present on the electrodes by means of two flanges 35, apt to guarantee an optimal sealing.

The first interlocking coupling 4 is finally completed by an inner body 5, preferably made of a tongue of a polymeric material. In particular it is made of a fiberglass printed circuit which will be better explained hereafter. Such inner body 5 is apt to be inserted into the inner cavity 30 and to prevent for interference the elastic deformation of the deformable portions 31 of the junction element 3, and preferably of the arms 32, in such a way as to prevent the releasing of the first interlocking coupling 4 (FIG. 4).

Furthermore, the electrodes 2 are preferably made of a conductive portion 21, made of a metalized and preferably gold-plated polymer, and an insulating portion 22, made of insulating polymeric material. Such portions 21 and 22 are mutually coupled through a second interlocking coupling 6. The coupling of the two portions 21 and 22 is made fluid-tight by means of a gasket 23, interposed at the outer surface of the electrode 2.

Figure 3A:
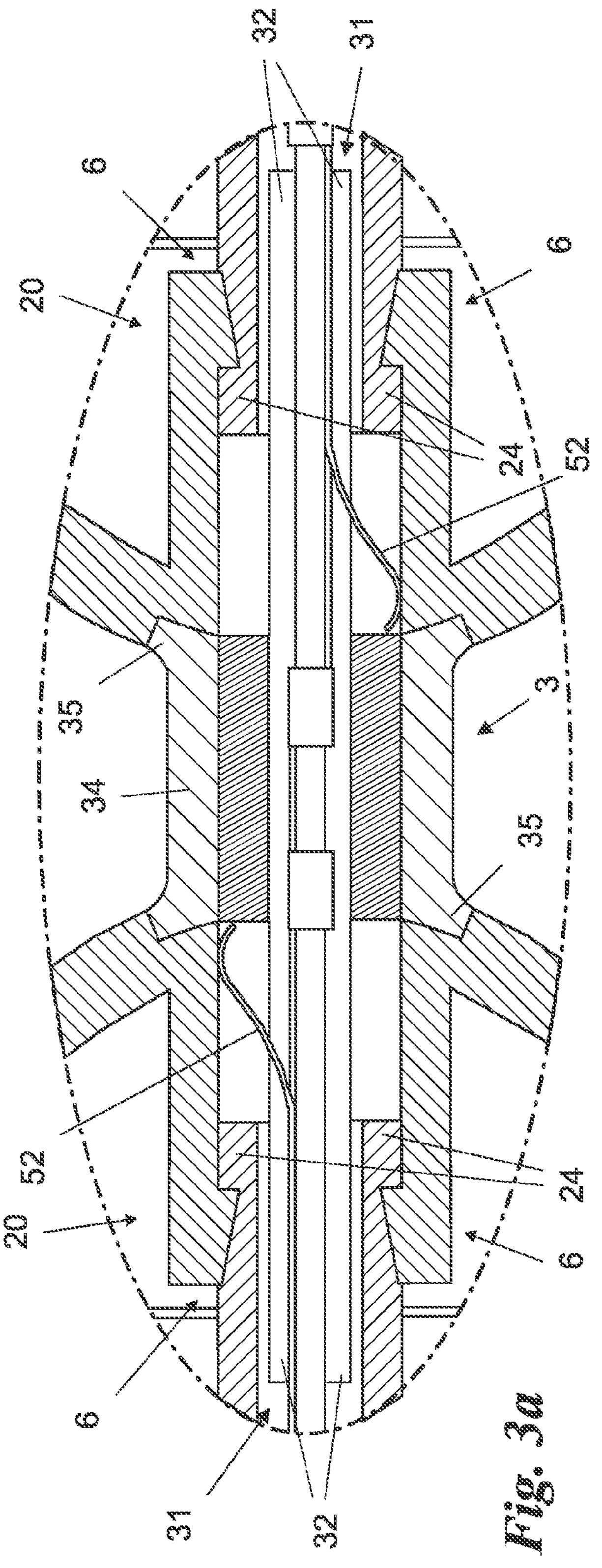
FIG. 3*a* is a magnification of FIG. 3.

The second interlocking coupling 6 (FIG. 3*a*) is preferably provided at the seat 20, where also the first interlocking coupling 4 is realized. It is preferably obtained by means of deformable elements 24 mainly extending parallel to the front plane 1*b*, spaced along the sagittal plane 1*c* (FIG. 1 and FIG. 3) and deflectable towards the interior of the element 24, in order to permit the second interlocking coupling 6.

Furthermore, the junction element 3, when inserted into the seat 20, is apt to prevent the elastic deformation of the elements 24, in particular through the arms 32, in order to prevent the release of the second interlocking coupling 6.

In particular, the second interlocking coupling is made of the seat 20, placed on the conductive portion 21 and made of the lateral surface of a cylindrical element with an elliptical base profile and provided at the sagittal plane (FIG. 3) with abutments for the second interlocking coupling 6.

The insulating portion 22 comprises instead two sectors of a cylindrical lateral surface, provided with teeth, apt to be inserted into the cylindrical element and be blocked at the abutments (FIG. 3).

The two interlocking couplings 4 and 6 so act along substantially perpendicular surfaces. This implies that the first interlocking coupling 4 can be inserted into the second interlocking coupling 6, by blocking it and permitting to the inner body 5 to block both couplings 4 and 6.

Preferably the inner body 5 substantially extending along the length of the probe 1 (FIG. 3 and FIG. 4) comprises electrical connections 51, apt to connect the conductive portions 21 with the outer electrical connections 8. The electrical connections are substantially made of a printed circuit integrated with cantilever conductive elements 52 (FIG. 3) protruding from said inner body 5 and apt to contact the inner portion of the seat 20.

The two conductive cantilevers 52 are also elastic in order to be flexible in the direction of insertion into the probe 1, starting from the handle 7 to the electrodes 2 and in order to be extracted with difficulty, if not to completely prevent the extraction of the inner body 5 from the probe 1.

For the same purpose the inner body 5 also comprises blocking elastic elements 53 (FIG. 4) which in the way explained before make that the insertable body 5 cannot be extracted from the probe 1, in particular due to the presence of steps 25, placed in the insulating portion 22 of the electrode 2 adjacent to the handle 7. For reason of constructive economy, the blocking elastic elements 53 are made of the same material and are made in a single piece with the printed circuit and the elements 52.

The inner body 5 is then fixed with a terminal portion 54 attached to the handle for interlocking or preferably for bonding.

The handle 7 is preferably integral in a single piece with the insulating portion 21 of one of said electrodes 2.

Figure 1:
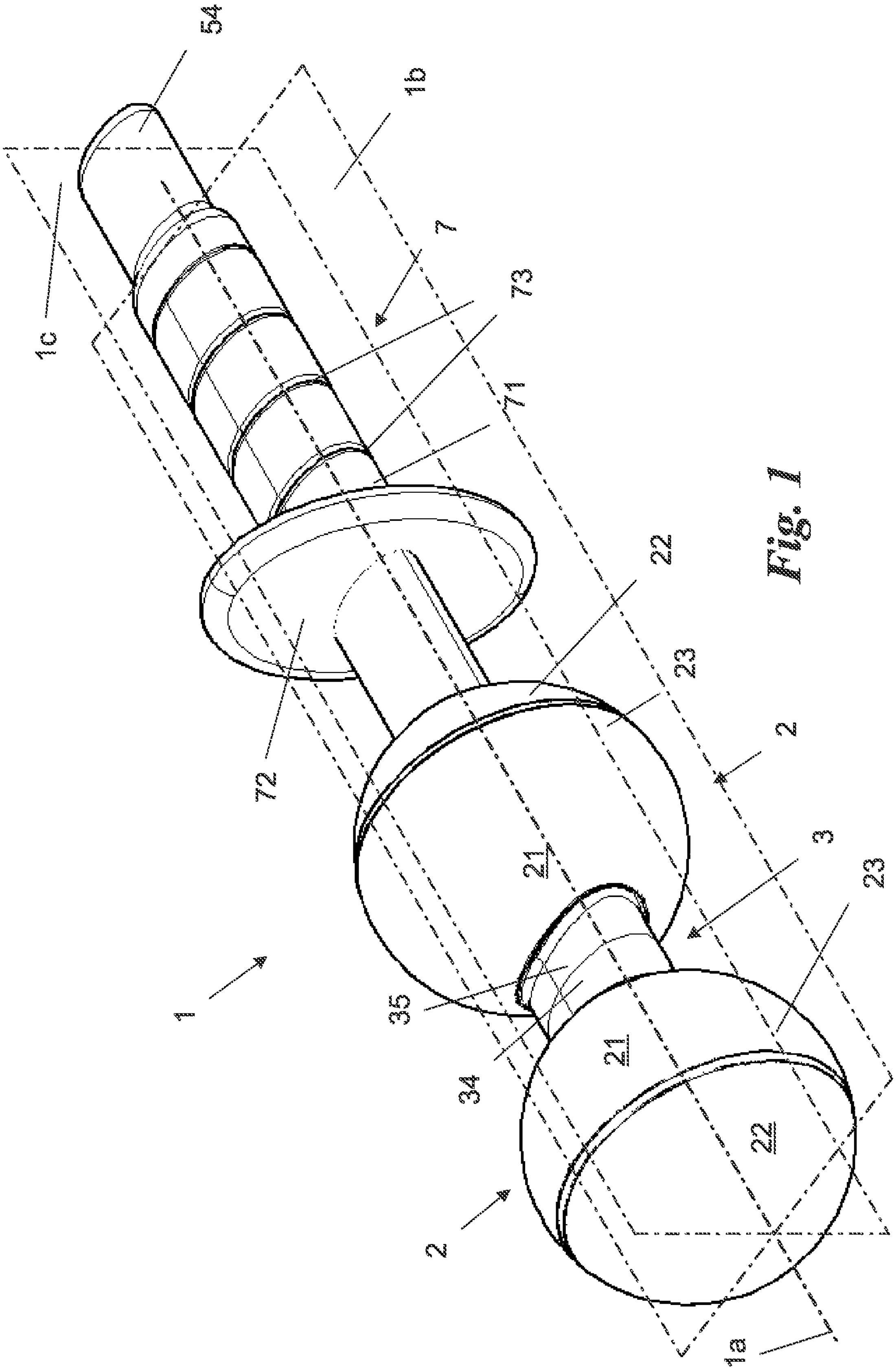
FIG. 1 shows a perineal probe according to the invention in an axonometric view.

The same handle 7 comprises a covering element 71 made of an elastic and soft material, surrounding the handle in its outer part and provided with a retaining flange 72, at the electrodes 2. The position of the flange 72, determined by the length of the covering element 71, can further be controlled, in particular through the presence of manually releasable sectors by braking, along suitable blanking lines 73 (FIG. 1).

The invention further comprises a novel method for making a perineal probe 1.

Such method is suitably obtained through the perineal probe 1 described before and illustrated in the annexed figures.

Said method provides for the composition of the electrodes 2 by interlocking, through the second interlocking coupling 6, of the conductive portions 21 with the insulating portions 22 and also with the gasket 23.

The same method also provides for the interlocking coupling, through said two first interlocking couplings 4, of the junction element 3, made of the tightening portion 34 and of the connecting portion 33, with the electrodes 2.

Following said last coupling, disassembling the single portions making the electrodes is made impossible due to the fact that the junction element 3, when inserted into the seat 20, is apt to prevent the elastic deformation of the elements 24, in particular by means of the arms 32, so as to prevent the release of the second interlocking coupling 6 (FIG. 3).

Subsequently the covering element 71 and the inner body 5 are inserted.

The latter is preferably bonded with the handle 7 at the end portion 54.

The inner body 5 is inserted in the interior of the probe 1 as a whole, and prevents the release of the first interlocking couplings 4, and so prevents the separation between the electrodes 2 and the junction element This is because the inner body 5 hinders the elastic deformation of the deformable portions 31 of the junction element 3, and preferably of the arms 32, in such a way to prevent the release of the first interlocking coupling 4 (FIG. 4).

The inner body 5 is further blocked by the bonding and the elastic blocking elements 53. It further provides for the electrical connection among the conductive portions 21 of the electrodes 2 and the outer electrical connections 8 through the cantilevered conductive elements 52 and the printed circuits making the electrical connections 51.

The use of the perineal probe 1 is similar to using the probes of the known type, with the difference that, before the first use of the probe 1 itself the position of the retaining flange 72 can be regulated eventually by removing the sectors defined by the blanking lines 73.

The invention permits important advantages.

The probe 1 in fact is simple and economical. It is in fact assembled very quickly, due to the fact that it is mainly made of interlocking couplings, which can be made much more quickly with respect to bonding or welding.

Furthermore the single elements can be made of a polymeric material and so they are cheap and light.

The conductive portion 21 of the electrodes 2 can be made of a polymeric material and are metalized through known methods, then gold-plated or with other metal, without implying the metallization of further portion, as to further reduce the costs.

The invention is susceptible of changes within the field of the inventive concept expressed by the independent claims. For example the connecting portion 32 can be made of a single piece with the insulating portion 22 of the first electrode.

All described and claimed elements can be substituted with equivalent elements and details, materials, shape and dimensions can be of any kind, within the scope defined by the independent claims.

The invention claimed is:

1. A perineal probe extending along a main axis in an axial direction, comprising:
- at least two electrodes protruding from said axial direction, spaced apart from one another and electrically insulated along said axial direction;
- an inner body; and
- a junction element configured to mechanically connect said at least two electrodes and extending along said main axis in said axial direction, at least one of said at least two electrodes comprising a seat for said junction element to form a first interlocking coupling between said junction element and said seat, said junction element comprising
  - an inner cavity extending along said main axis in said axial direction, and
  - elastically deformable portions configured to form said first interlocking coupling, and said inner body is configured to be inserted in said inner cavity and configured to prevent interference with elastic deformation of said elastically deformable portions of said junction element in order to prevent the release of said first interlocking coupling.

2. The perineal probe according to claim 1, wherein said at least two electrodes each comprise a conductive portion and an insulating portion, said portions being coupled by a second interlocking coupling.

3. The perineal probe according to claim 2, wherein said second interlocking coupling is provided at said seat.

4. The perineal probe according to claim 3, wherein said first interlocking coupling introduced into said seat prevents the release of said second interlocking coupling.

5. The perineal probe according to claim 2, wherein said second interlocking coupling is achieved by deformable elements defining an interior, said deformable elements bending towards said interior, in order to allow for said second interlocking coupling.

6. The perineal probe according to claim 2, further comprising a handle, integrated as a single piece with the insulating portion of one of said electrodes.

7. The perineal probe according to claim 2, wherein said inner body, substantially extending along said probe as a whole, comprises electrical connections with said conductive portions, and with an outer portion of said perineal probe.

8. The perineal probe according to claim 2, wherein said first and said second interlocking couplings act along substantially perpendicular surfaces.

9. The perineal probe according to claim 1, wherein said first interlocking coupling comprises
- a hollow sealing portion,
- a connecting portion configured for being introduced into said hollow sealing portion and configured to mechanically connect said two electrodes, and
- a tightening portion made of a flexible material and configured to provide a liquid-tight connection between said junction element and said electrodes.

10. A method for making a perineal probe according to claim 3, comprising:
- interlocking said conductive portions with said insulating portions of each of said electrodes to form said second interlocking coupling;
- interlocking said junction element with said electrodes to form said first interlocking coupling;
- inserting said inner body into said inner cavity; and
- bonding said inner body with a handle.

* * * * *